US005750995A

United States Patent [19]
Clarke

[11] Patent Number: 5,750,995
[45] Date of Patent: *May 12, 1998

[54] METHODS AND DEVICES FOR FUEL CHARACTERIZATION AND OPTIMAL FUEL IDENTIFICATION ON-SITE AT A FUEL DELIVERY DISPENSER

[75] Inventor: Richard H. Clarke, Big Sky, Mont.

[73] Assignee: Boston Advanced Technologies, Inc., Marlborough, Mass.

[*] Notice: The term of this patent shall not extend beyond the expiration date of Pat. No. 5,569,922.

[21] Appl. No.: 601,337

[22] Filed: Feb. 16, 1996

[51] Int. Cl.$^6$ .......................... G01N 21/35; G01N 33/22
[52] U.S. Cl. ..................... 250/339.12; 250/339.09
[58] Field of Search ................. 250/339.12, 343, 250/339.11, 339.09

[56] References Cited

U.S. PATENT DOCUMENTS

| | | |
|---|---|---|
| 3,973,848 | 8/1976 | Jowett et al. . |
| 4,323,777 | 4/1982 | Baskins et al. . |
| 4,620,284 | 10/1986 | Schnell et al. . |
| 4,934,419 | 6/1990 | Lamont et al. . |
| 4,963,745 | 10/1990 | Maggard . |
| 5,046,355 | 9/1991 | Tack et al. . |
| 5,126,570 | 6/1992 | Boos . |
| 5,139,334 | 8/1992 | Clarke . |
| 5,205,151 | 4/1993 | Shimamura et al. . |
| 5,225,679 | 7/1993 | Clarke et al. . |
| 5,412,581 | 5/1995 | Tackett . |
| 5,430,295 | 7/1995 | Le Febre et al. . |
| 5,569,922 | 10/1996 | Clarke ............................. 250/339.12 |

FOREIGN PATENT DOCUMENTS

| | | |
|---|---|---|
| 0285251 | 10/1988 | European Pat. Off. . |
| 0 305 090 | 3/1989 | European Pat. Off. . |
| 197810 | 10/1978 | United Kingdom . |
| WO 92/21971 | 12/1992 | WIPO . |

OTHER PUBLICATIONS

*Changes in Gasoline II*, Downstream Alternatives, Inc., Bremen, IN, Jul. 1992.

Kelly et al., "Prediction of Gasoline Octane Numbers from Near–Infrared Spectral Features in the Range of 660–1215 nm," *Analytical Chemistry*, 61:4, 313–320 (Feb., 1989).

Louw and Richards, "A Simple Directly Combined Gas Chromatographic–Infrared Spectrometric System for Identification of Low Molecular Weight Hydrocarbons," *Applied Spectroscopy*, 29:1, 15–24 (1975) no month.

Telfair et al., "A microcomputer–controlled infrared analyzer for multi–component analysis," *American Laboratory*, 8:11, 91–100 (Nov., 1976).

*Primary Examiner*—Edward J. Glick
*Attorney, Agent, or Firm*—Thomas J. Engellenner; C. Eric Schulman; Lahive & Cockfield, LLP

[57] ABSTRACT

Method and devices for fuel characterization and optimization on-site at a fuel delivery dispenser are disclosed. Fuel properties associated with a fuel sample of a fuel can be measured by mid-infrared analysis and displayed. Predetermined preferred values for the fuel properties for the particular vehicle can be determined by inputting the model and type of vehicle into a processing means and correlating the vehicle information with the preferred values. The preferred and measured values can be compared and the comparison displayed. A fuel sample rating for the vehicle can be performed based this comparison and displayed. An optimal dispenser fuel for the vehicle can be identified based on a comparison between the preferred values and the values for the fuel properties for each of the dispenser fuels. In one embodiment, driveability index can be the fuel property determined in situ and in real time. In other embodiments, octane number, and Reid vapor pressure can be similarly determined.

27 Claims, 4 Drawing Sheets

```
                    GM GOODWRENCH
                 AUTO FUEL EVALUATION
                    CHECKOUT SHEET

VEHICLE TYPE:  SATURN SLI
              MODEL:         1993-1994
              TEST TIME:     6:09:30 P.M.
              TEST DATE:     2/27/95

FUEL PROPERTY     VALUE    SPEC. VALUE

OCTANE (R+M/2)     87      87 OR HIGHER
    DRIVABILITY       1350     1200 OR LOWER
    RVP (PSI)           9      NO SPEC.
    ETOH (VOL %)        0      10% MAX.
    ETOH (VOL %)        0      10% MAX.
    MEOH (VOL %)        0      LESS THAN 4%
    MTBE (VOL %)        5      LESS THAN 15%
    ETBE (VOL %)        0      NO SPEC.
    TAME (VOL %)        0      NO SPEC.
    TBA (VOL %)         0      NO SPEC.
    DIPE (VOL %)        0      NO SPEC.
    OLE (VOL %)         0      NO SPEC.
    Wt. % OXY          1.1

OVERALL FUEL QUALITY:
    MARGINAL - DRIVABILITY VALUE INDICATES POTENTIAL
           COLD STARTING PROBLEMS.
```

METHODS AND DEVICES FOR FUEL CHARACTERIZATION AND OPTIMAL FUEL IDENTIFICATION ON-SITE AT A FUEL DELIVERY DISPENSER

BACKGROUND OF THE INVENTION

The field of the present invention is fuel characterization and optimal fuel identification. In particular, the present invention involves methods and devices for the characterization of a fuel sample on-site at a fuel delivery dispenser and the identification of an optimal fuel choice for the vehicle.

In many cases, vehicle operators experience less than optimal vehicle performance because of their choice of engine fuel for a particular vehicle. Methods and devices for the characterization of a fuel sample and the identification of the optimal fuel choice for the vehicle based on the vehicle manufacturer's fuel recommendations, are, however, typically unavailable at the fuel delivery dispenser, where if such identifications could be made, the appropriate fuel could be added to the vehicle.

Different methods and devices exist for the characterization of hydrocarbon fuels. For example, some methods and devices involve the determination of a value for octane number. Octane number is a measure of a fuel's ability to resist engine knocking. Engine knocking results when a fuel fails to burn smoothly and evenly, and the resulting unburned portion of the air/fuel mixture explodes violently from spontaneous combustion. Octane number is conventionally determined and stated according to ASTM methods. For example, a research octane number (RON) can be determined according to ASTM Method 2699-84, and a motor octane number (MON) can be determined according to ASTM Method 2700-84. The conventional octane ratings for delivery dispenser fuels are determined as one-half the sum of RON plus MON.

Other methods and devices for the characterization of hydrocarbon fuels involve the determination of Reid vapor pressure. Reid vapor pressure is a measure of a fuel's "front end volatility" or more volatile components. It can be measured by performing a "Reid Method" test procedure whereby a gasoline sample, which is sealed in a metal chamber, is submerged in a 100° F. water bath. Higher readings are determined for the more volatile fuels because such components vaporize more readily, thus creating more pressure on the measurement device. Lower readings are determined for the less volatile fuels because such components create less vapor.

Various other methods are known for the evaluation of octane number, Reid vapor pressure and other fuel properties. Notwithstanding, analytical tools employing these methods are typically not available at the fuel delivery dispenser for measuring the properties of a fuel sample, comparing such results with the manufacturer's fuel recommendations for the vehicle, and identifying the optimal fuel choice for the vehicle based upon the fuel choices available at the dispenser. Accordingly, there exists a need to provide simple and relatively inexpensive methods and devices at the fuel delivery dispenser for quickly and accurately characterizing a fuel sample and identifying the optimal fuel for a particular vehicle.

SUMMARY OF THE INVENTION

The present invention is based on the recognition that a fuel can be simply and relatively inexpensively characterized on-site at a fuel delivery dispenser by using mid-infrared analysis to measure fuel properties, such as driveability index, of a sample of the fuel. These measured values can be compared with the preferred property values for a particular vehicle based on the manufacturer's fuel recommendations. Further, the optimal fuel choice for the vehicle can be identified by correlating the preferred property values with the values for the property for each of the fuels available at the dispenser.

Accordingly, in one aspect of the invention, selected fuel properties associated with a fuel sample of a select fuel (including, but not limited to, any fuel available at the dispenser) can be measured on-site with mid-infrared analysis and displayed. The term "on-site", as used herein, refers to a location at or near a fuel delivery dispenser. Such dispensers can be located at gasoline service stations, convenience stores or other locations where gasoline is provided to consumers. The term "display", as used herein, describes a transient visual display as well as other more permanent records, such as hard copy print outs, which can be displayed to the vehicle operator and/or fuel service provider.

In one embodiment, the measured fuel property values for the sample can be compared with pre-determined preferred value ranges for the fuel properties for the sample based upon the fuel company's specifications for the fuel, and the result of the comparison displayed. In another embodiment, a rating for the fuel sample can be evaluated based upon this comparison, and displayed.

In other embodiments, vehicle information, such as model and type of vehicle, can be entered; pre-determined preferred value ranges for the fuel properties for the particular vehicle can be determined based upon the vehicle manufacturer's fuel recommendations; the measured values for the fuel sample can then be compared with these pre-determined preferred value ranges; and the comparison can be displayed. A rating for the fuel sample can then be evaluated based upon this comparison between the preferred and measured values, and displayed.

In still other embodiments, the pre-determined preferred value ranges for the fuel properties can be correlated with values for the fuel properties for each of the dispenser fuels, and an optimal dispenser fuel for the vehicle identified and displayed based upon this correlation. The term "dispenser fuel(s)", as used herein, refers to the fuels available at the fuel delivery dispenser.

In one embodiment of the invention, a driveability index can be one of the fuel properties which is measured and used to characterize the fuel sample. Driveability indices are conventionally determined and stated according to the known ASTM D-86 method. According to this method, three distillation temperatures, T10, T50, and T90 are determined for a sample. T10, T50, and T90 correspond to the temperatures at which 10 percent, 50 percent, and 90 percent, respectively, of the sample are distilled off. The derivability index for the sample is then determined according to the following equation:

$$\text{Driveability index} = 1.5 \ (T10) + 3.0 \ (T50) + 1 \ (T90)$$

In contrast to the conventional methods for measuring driveability index, an embodiment of the invention involves measuring fuel properties, such as driveability index, by illuminating a fuel sample with mid-infrared light and detecting absorbance values associated with the components of the fuel. The detected absorbance values can be correlated with a matrix of pre-determined coefficients associated with the fuel components and pre-determined values of the fuel property. The detected absorbance values can be multiplied by their corresponding pre-determined coefficients and the resulting absorbance-coefficient products can be summed to determine the value of the fuel property, such as driveability index, associated with the sample.

Alternatively, in another embodiment of the invention, detected absorbance values for a fuel sample can be correlated with a matrix of pre-determined coefficients associated with the fuel components of the sample and pre-determined T10 values. The detected absorbance values can be multiplied by their correlated pre-determined coefficients and the resulting absorbance-coefficient products can be summed to determine a T10 value associated with the sample. Similarly, detected absorbance values can be correlated with matrices of pre-determined coefficients associated with the fuel components of the sample and pre-determined T50 and T90 values. The detected absorbance values can be multiplied by their correlated pre-determined coefficients and the resulting absorbance-coefficient products can be summed to determine T50 and T90 values for the sample. The determined T10, T50 and T90 values can then be inserted into the standard driveability index equation to obtain a driveability index associated with the sample.

In further embodiments of the invention, fuel properties such as octane number and Reid vapor pressure can be determined and used to characterize the engine fuel.

The invention further encompasses analytical devices for measuring pre-selected fuel properties associated with a fuel sample of a select fuel (including, but not limited to, the available dispenser fuels). The devices can include a sample measurement means for measuring on-site fuel property values associated with the sample through mid-infrared analysis; and a display means for displaying the measured fuel property values.

In one embodiment, the devices can further include a comparison means for comparing these measured fuel property values with pre-determined preferred value ranges for the fuel properties based upon the fuel company's specifications for the fuel; and a display means for displaying a result of this comparison. In another embodiment, the devices can further include a rating means for evaluating the fuel sample based upon the comparison between the measured values and the pre-determined preferred value ranges for the fuel properties for the sample; and a display means for displaying the fuel sample rating.

In other embodiments, the devices can further include an inputting means for entering vehicle information, such as the model and type of vehicle; a processing means for correlating vehicle information with pre-determined preferred value ranges for the fuel properties based upon the manufacturer's fuel recommendations for the particular vehicle; and a comparison display means for comparing the measured values with the pre-determined preferred value ranges, and displaying the result of the comparison. The devices can further include a rating means for evaluating a rating for the fuel sample based upon the comparison; and a rating display means for displaying the fuel sample rating.

In still other embodiments, the devices can further include an optional alternative dispenser fuel identification means for correlating the pre-determined preferred value ranges with values for the fuel properties for each of the dispensers fuels to identify the optimal dispenser fuel choice for the vehicle; and an optimal alternative dispenser fuel display means for displaying the optimal dispenser fuel choice.

In further embodiments of the invention, the measurement means can further include a driveability index determination means for determining driveability index. The measurement means can include a mid-infrared light source for illuminating the sample; a detector for detecting absorbance values associated with fuel components; a correlating means for correlating the detected absorbance values with a matrix of pre-determined coefficients associated with the fuel components and pre-determined values of the fuel property; a multiplying means for multiplying the detected absorbance values by their correlated pre-determined coefficients; and a summing means for summing the resulting absorbance-coefficient products to determine a value for a fuel property, such as driveability index, associated with the sample.

In still a further embodiment, the driveability index measurement means can include a mid-infrared light source for illuminating the sample; a detector for detecting absorbance values associated with fuel components; a correlating means for correlating the detected absorbance values with a matrices of pre-determined coefficients associated with the fuel components and pre-determined T10 values, T50 values, and T90 values; a multiplying means for multiplying the detected absorbance values by their correlated predetermined coefficients; a summing means for summing the resulting absorbance-coefficient products to determine values of T10, T50 and T90 associated with the sample, and a determination means for determining the driveability index of the sample based upon the determined T10, T50 and T90 values.

In other embodiments, the measurement means can further include an octane number determination means for determining octane number and/or a Reid vapor pressure determination means for determining the Reid vapor pressure. The devices of the present invention can be portable and/or an integral part of the fuel delivery dispenser. The devices of the present invention can further include a data communication means for communicating with a remote computer.

BRIEF DESCRIPTION OF THE DRAWINGS

These and other features and advantages of the present invention will be more fully understood by reference to the following detailed description in conjunction with the attached drawings in which like reference numerals refer to like elements and in which.

DETAILED DESCRIPTION OF THE INVENTION

Figure 1:
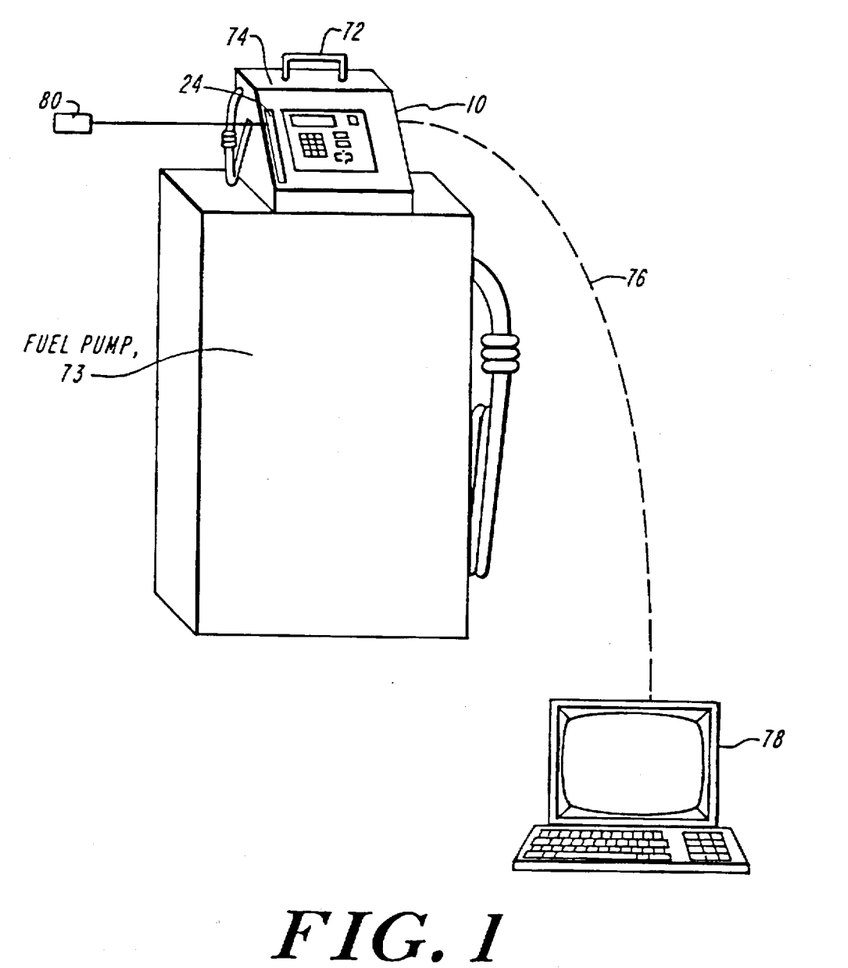
FIG. 1 illustrates an exterior view of a fuel characterization and optimal fuel identification device for characterizing a fuel sample on-site at a fuel delivery dispenser and for identifying an optimal dispenser fuel for the vehicle, according to an embodiment of the invention.

FIG. 1 is a schematic of an exterior view of a fuel characterization and optimal fuel identification device 10, according to an embodiment of the invention. The device 10 can be an integral part of the fuel delivery dispenser 73. Alternatively, the device 10 can be portable and can be carried by handle 72. In either case, the device 10 can be encased in a material 74 that can have the resilience and durability for use on-site at a fuel delivery dispenser. The device 10 can also be equipped with the means 76 for communicating with a remote computer 78. FIG. 1 further illustrates the inputting means 24 for entering vehicle information from a personal information card 80 containing vehicle model and type information.

Figure 2:
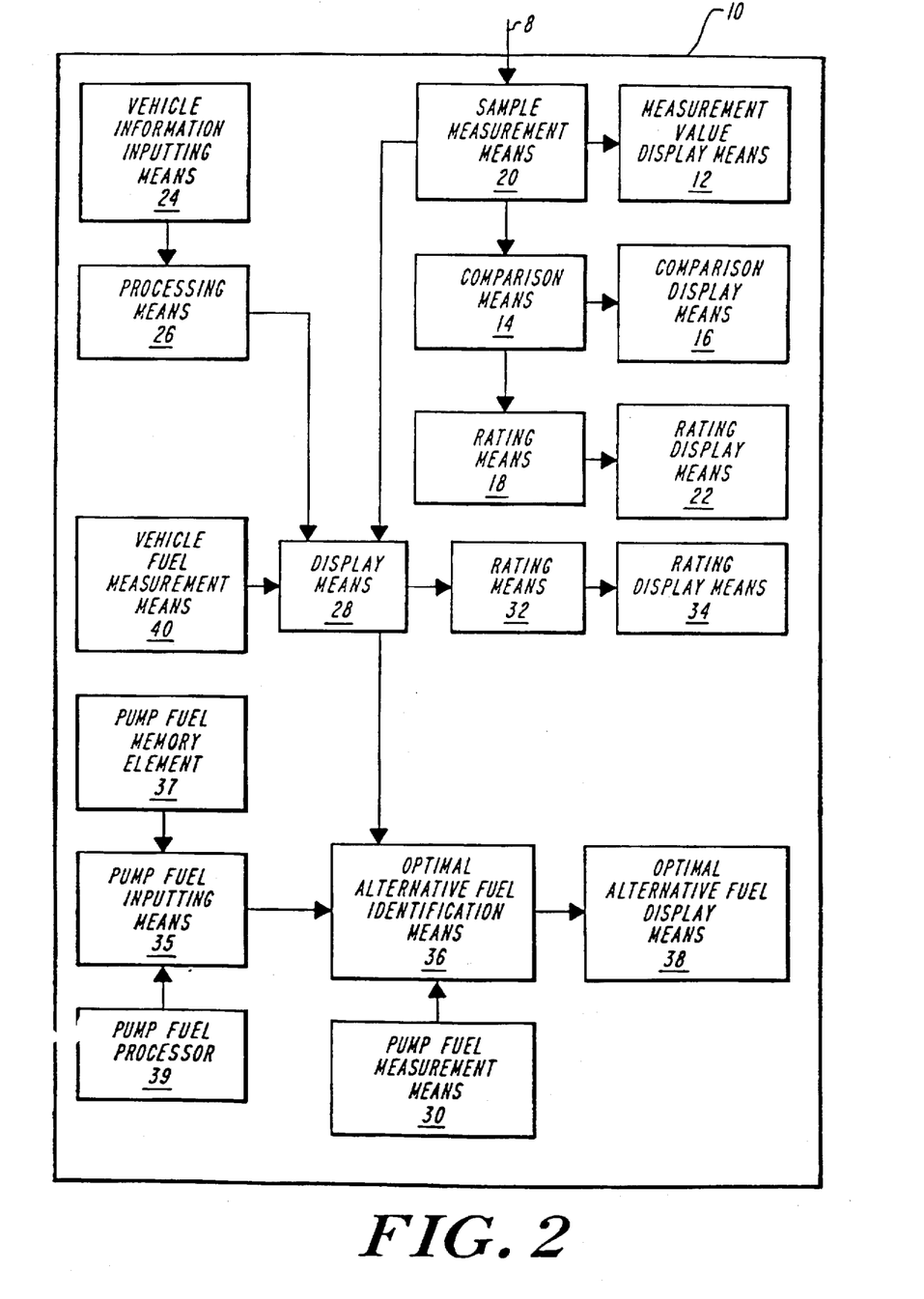
FIG. 2 is a schematic representation of a fuel characterization and optimal fuel identification device for characterizing a fuel sample on-site at a fuel delivery dispenser and for identifying an optimal dispenser fuel for the vehicle, according to an embodiment of the invention.

FIG. 2 is a schematic representation of a fuel characterization and optimal fuel identification device 10 for characterizing on-site a fuel sample 8 from a dispenser or a storage tank and for identifying an optimal dispenser fuel for the vehicle, according to an embodiment of the invention. The device 10 illustrated in FIG. 2 is equipped with a sample measurement means 20; a measurement value display means 12; a comparison means 14; a comparison display means 16; a rating means 18; and a rating display means 22. The device 10 can further include a vehicle information inputting means 24; a processing means 26; a display means 28; a rating means 32; and a rating display means 34. In yet another embodiment of the invention, the device 10 can further include a dispenser fuel measurement means 30; a dispenser fuel inputting means 35; an optimal alternative fuel identification means 36; a dispenser fuel memory element 37; an optimal alternative fuel display means 38; and a dispenser fuel processor 39. In a further embodiment, the device 10 can include a vehicle fuel measurement means 40.

In the practice of the invention, values for selected fuel properties of the sample 8 from a fuel dispenser or storage tank can be measured on-site through mid-infrared analysis with the sample measurement means 20 and then fed into the measurement value display means 12 and displayed.

The measured fuel property values of the sample 8 can be fed into the comparison means 14 and compared with pre-determined preferred value ranges for the fuel properties for the fuel sample based on the fuel company's specifications for the fuel. The result of the comparison can be displayed with display means 16.

The measured values and pre-determined preferred value ranges can also be fed into a rating means 18 which can evaluate a rating for the fuel sample 8 based on the comparison between the measured and preferred fuel property values. This rating for the fuel sample 8 can be displayed with the rating display means 22. For example, the display means 22 can display an "UNACCEPTABLE FUEL QUALITY" message, where the measurement means measures a drivability index of 1350 for a fuel sample, and the preferred pre-determined drivability index range for that fuel is 1100–1200.

The desired fuel characteristics for a particular vehicle can also be determined and compared with the measured characteristics of the fuel at the fuel delivery dispenser. Vehicle information, such as the model and type of vehicle, can be entered into the processing means 26 via the inputting means 24. The processing means 26 can correlate the vehicle identification information with the pre-determined preferred values for the fuel properties for the vehicle in a look-up table. The sample and pre-determined preferred fuel property values can then be fed into, compared and the comparison displayed with the comparison display means 28.

Various devices and/or methods can be used for inputting the vehicle information via the inputting means 24. For example, the relevant vehicle information can be entered manually by the vehicle operator or fuel service provider. Alternatively, the vehicle information can be entered by inserting a type of personal information card (with vehicle information encoded on a magnetic stripe or the like) into the inputting means 14 which can then read the relevant information off the card.

The measured values and the preferred value ranges of the fuel properties can be fed into a rating means 32 to evaluate the fuel sample based upon a comparison between the measured values and the preferred pre-determined value ranges for the vehicle. In one embodiment, the rating means 32 can calculate a difference between the measured value and the closest value of the pre-determined preferred ranges for each of the selected fuel properties. Such differences can be fed into a rating display means 34 for display of fuel sample rating messages. For example, the rating display means 34 can display a message such as "Sample DI: 23% Higher than Recommended DI for Vehicle."

Alternatively, the rating means 32 can correlate the difference between the measured values and preferred values for the vehicle with a qualitative rating in look-up table. The information can be fed into the fuel sample rating display means 34 which can display a qualitative fuel sample message based on the correlation. Examples of qualitative messages include, but are not limited to, "FUEL QUALITY FOR VEHICLE: Excellent, Good, Average, or Marginal."

The fuel properties' pre-determined preferred value ranges for the vehicle can also be fed into an optimal alternative dispenser fuel identification means 36. For each of the selected properties, the optimal alternative dispenser fuel identification means 36 can compare the pre-determined preferred value range with the values for the properties for each of the dispenser fuels. The optimal alternative dispenser fuel identification means 36 can then identify the dispenser fuel with the closest property value to the pre-determined property value range for the fuel property. The optimal alternative dispenser fuel choice can be displayed with the alternative optimal dispenser fuel display means 38. For example, the optimal alternative dispenser fuel display means can display a message such as "OPTIMAL FUEL CHOICE: Dispenser Fuel #3."

Various devices and/or methods can be used for inputting the pre-determined preferred value ranges for the fuel properties for each of the dispenser fuels into the optimal alternative fuel identification means 36. In one embodiment, the dispenser fuel measurement means 20 can be used for measuring through mid-infrared analysis values for the selected fuel properties for samples of each of the dispenser fuels, and these values can be fed into the optimal alternative fuel identification means 36. In another embodiment, a separate but similar infrared measurement means 30 can be used for measuring the dispenser fuel property values. In still another embodiment, values for the selected fuel properties of each of the dispenser fuels can be entered into the optimal alternative dispenser fuel identification means 36 via a dispenserfuel inputting means 35. The dispenser fuel property values provided by the dispenser fuel inputting means 35 can be from a dispenser fuel memory element 37, e.g., stored values from previous measurements, or from a dispenser fuel processor 39 which provides calculated values for blends. Once measured or inputted, the dispenser fuel property values can be fed into the optimal alternative fuel dispenser identification means 36.

FIG. 2 further illustrates that in other embodiments of the invention, the device 10 can include means for extracting a fuel sample from the vehicle and delivering it to a vehicle fuel measurement means 40 for measuring through mid-infrared analysis selected fuel properties of the sample. The measured values can be fed into the display means 28 for displaying a comparison between the measured values for the fuel sample from the vehicle and the pre-determined preferred values ranges for the fuel properties for the vehicle. The measured and preferred values for the fuel sample can be fed into the rating means 32, and the rating means 32 can evaluate a sample rating based upon the comparison between the measured values for the sample from the vehicle and the pre-determined preferred property values. Display means 34 can then display this fuel sample rating.

In still other embodiments, the rating means 32 can also correlate the difference between the actual and preferred fuel property values with a potential fuel-related problem in a look-up table. For example, if the actual driveability index of the fuel sample is 1350 and the preferred driveability index for the vehicle is 1100, the rating means 32 can determine that the comparison between actual and preferred driveability index values indicates a potential problem for starting in cold weather and the fuel sample rating display means 34 can display the result of this diagnosis. Table 1 provides a non-inclusive list of fuel properties, such as driveability index, which are relevant to particular fuel-related problems.

TABLE 1

FUEL PROPERTIES RELEVANT TO PARTICULAR FUEL-RELATED PROBLEMS

| Fuel Property | Fuel-Related Problem |
| --- | --- |
| Fuel Volatility | |
| Driveability Index | Cool weather driveability problems, hot start and hot driveability problems, vapor lock, evaporative losses, crankcase deposits, combustion chamber and spark plug deposits |
| Reid Vapor Pressure | Low temperature starting problems, evaporative losses, vapor lock |
| Vapor Liquid (V/L) Ratio | Vapor lock |
| Octane Number | |
| Research Octane Number (RON) | Low to medium speed knock and run-on |
| Motor Octane Number (MON) | High speed knock/Part-throttle knock |
| Copper Corrosivity | Fuel system corrosion |
| Stability | |
| Existent Gum | Induction system deposits, filter clogging |
| Oxidation Stability | Storage life limitations |
| Sulfur Content | Exhaust emissions, engine deposits and engine wear |
| Metallic additives (lead and others) | Catalyst deterioration (unleaded vehicles) |
| Temperature for Phase Separation | Water intolerance of blended fuels |

Figure 3:
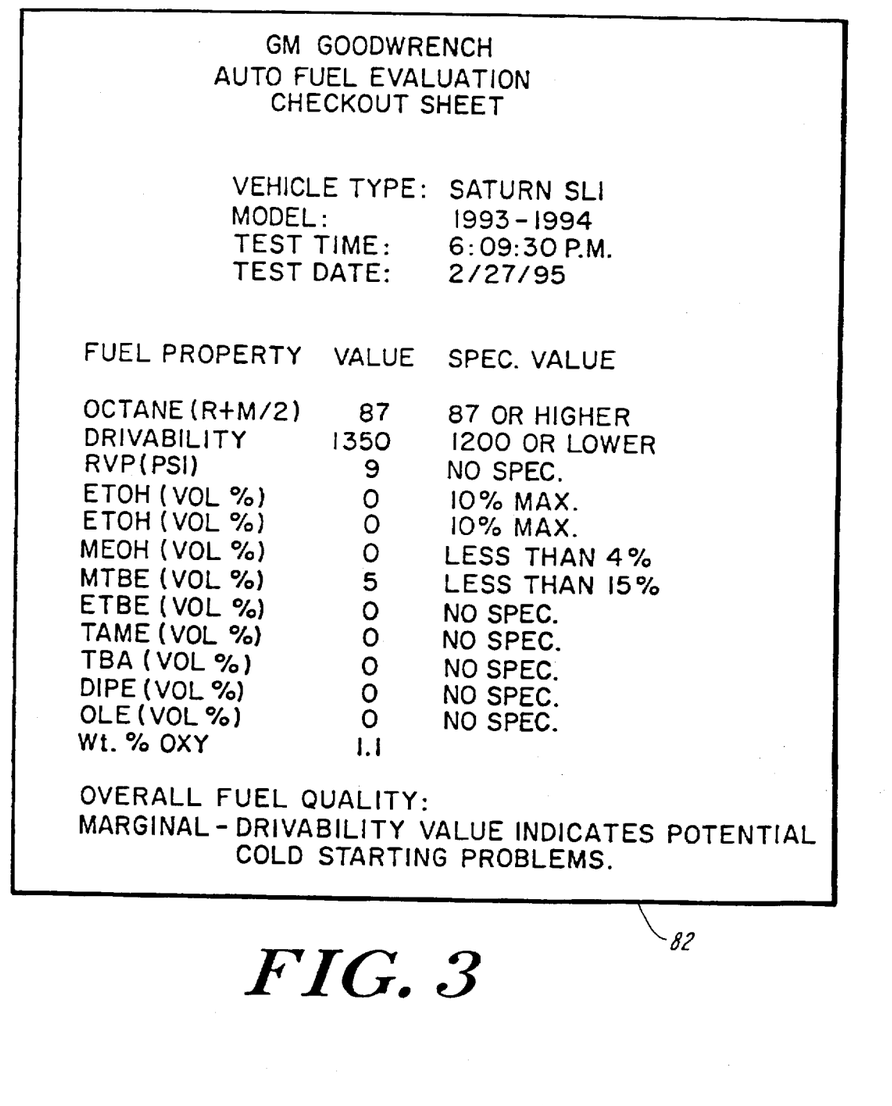
FIG. 3 is a view of a hard copy print out display from a comparison display means.

FIG. 3 is a view of a hard copy printout display 82 from comparison display means 28.

Figure 4:
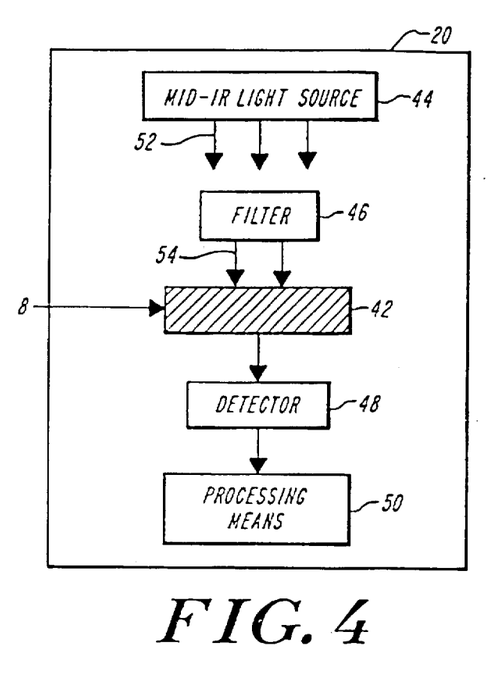
FIG. 4 is a more detailed schematic representation of the mid-infrared fuel properties measurement means of FIG. 1 for detection and evaluation of fuel properties of a fuel sample on-site at a fuel delivery dispenser, according to an embodiment of the invention.

FIG. 4 is a more detailed schematic representation of the mid-infrared fuel properties measurement means 20 for on-site detection and evaluation of components and properties of a fuel sample 8 of a select fuel from a dispenser or storage tank contained in an examination vessel 42, according to an embodiment of the invention. The measurement means 20 illustrated in FIG. 4 is equipped with a mid-infrared light source 44, a filter 46, a detector 48, and a processing means 50. The schematic representation of FIG. 4 also applies to dispenser fuel measurement means 30 and vehicle fuel measurement means 40.

Mid-infrared analysis in the practice of the present invention can involve illuminating a fuel sample with mid-infrared light in a range of about 2.5 μm to about 20 μm. The molecules of the fuel components of the sample can each exhibit characteristic primary, overtone and/or combination vibrational modes (also referred to herein as "signature" or "signature modes") when excited in narrow wavelength bandwidths associated with particular fuel components. These signatures can be exhibited in terms of absorbances of the mid-infrared light. Such absorbances can be detected and correlated with matrices of pre-determined coefficients associated with the fuel components and pre-determined fuel property values. The detected absorbance values can be multiplied by their correlated coefficients, and the resulting absorbance-coefficient products can be summed to determine property values associated with the sample.

For exemplary purposes, FIG. 4 illustrates a detector 48 assigned to methanol (MEOH) detection. Notwithstanding, in the practice of the invention, other detectors can be included and assigned specifically to the detection of ethanol (ETOH), tertiary butyl alcohol (TBA), Methyl tertiary butyl ether (MTBE), di-isopropyl ether (DIPE), ethyl tertiary butyl ether (ETBE), tertiary amyl methyl ether (TAME), metaxylene, toluene, and benzene. Further, two detectors can be assigned to the detection of aromatics since aromatic molecular structures can be detected at both shorter and longer wavelengths. Similarly, two detectors can be assigned to the detection of olefins which also can be detected at two different wave lengths. A separate detector can be assigned to the detection of straight chain hydrocarbons.

A separate detector can also be assigned to the detection of alkylates for use as a correction factor. A high percentage of alkylates in the fuel sample can raise the total absorbance spectrum and can lead to false readings for other fuel components (e.g., MBTE). Accordingly, the absorbance values for other fuel components can be adjusted to take into account the alkylates' effect once the alkylates' concentration is known.

Still another detector can be assigned as a reference detector for use as a correction factor. The reference detector can operate in that part of the absorbance spectrum where there is very little absorbance. Stated a little differently, the reference detector can operate in an "absorbance window". Some fuels can show absorbance in such an absorbance window, however. Thus, to normalize absorbance detection among various fuels, the absorbance values for the other fuel components can be adjusted to take into account absorbance detected in the absorbance window.

Alternatively, a single broad band detector can be used for the detection of multiple fuel components in the fuel sample.

In the embodiment of FIG. 4, the mid-infrared light source 44 can be provided on one side of the fuel-containing examination vessel 42 for illuminating the fuel sample 8 contained within the vessel. The detector 48 can be provided on the other side of the vessel 42 for the detection of absorption associated with the presence of the assigned fuel component. Because each detector of the invention can be assigned to a specific fuel component of interest, each detector's input can be limited to that narrow portion of the mid-infrared spectrum which is associated with a selected vibrational mode signature and which has been determined to be characteristic of the assigned fuel component.

Isolation of each detector to an assigned fuel component can be achieved in this embodiment by interposing the filter 46 between the light source 44 and the examination vessel 42. Light 52 from the mid-infrared light source 44 can enter the filter 46 and a narrow vibrational mode or wavelength 54 appropriate for the assigned fuel component being measured can exit the filter to enter the examination vessel 42. Table 2 shows an exemplary array of such filters.

TABLE 2

FUEL COMPONENT FILTER ARRAY

| Fuel component | Filter No. | Center Wavelength, $\lambda_c$ µm | Bandwidth 1% of $\lambda_c$ µm | Center Frequency cm$^{-1}$ |
|---|---|---|---|---|
| Reference | 17 | 4.80 | .0480 | 2083 |
| MEOH | 1 | 9.70 | .0970 | 1031 |
| ETOH | 2 | 9.52 | .0952 | 1054 |
| TBA | 3 | 10.93 | .1093 | 915 |
| MTBE | 4 | 8.30 | .0830 | 1205 |
| DIPE | 5 | 8.63 | .0863 | 1159 |
| ETBE | 6 | 8.95 | .0895 | 1117 |
| TAME | 7 | 8.42 | .0842 | 1188 |
| Gen. Arom. 1 | 8 | 6.23 | .0623 | 1605 |
| Metaxylene | 9 | 13.53 | .1353 | 739 |
| Toluene | 10 | 13.72 | .1372 | 729 |
| Benzene | 11 | 14.79 | .1479 | 676 |
| Gen. Arom. 2 | 12 | 13.00 | .1300 | 769 |
| Alkylate Corr | 13 | 7.32 | .0732 | 1366 |
| Olefins | 14 | 10.35 | .1035 | 966 |
| Straight Chain HCs | 15 | 3.51 | .0351 | 2852 |
| Olefins | 16 | 6.06 | .0606 | 1650 |

Additional filters and detectors can be employed for the detection of the other above-identified fuel components of interest. In addition, each filter can take the form of a window on a detector device itself, rather than as a separate discrete component. Further, the filter can even be eliminated where the detection is otherwise limited to a narrow band of interest.

Figure 5:
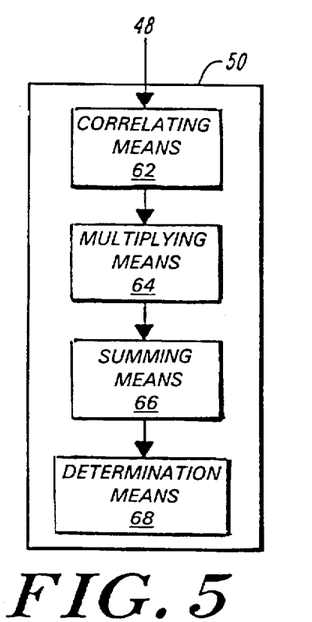
FIG. 5 is a more detailed schematic representation of the processor of FIG. 2 for processing of absorption detection signals to determine values for fuel properties associated with a fuel sample, according to an embodiment of the invention.

FIG. 5 is a detailed schematic representation of a processor 50 for processing absorption detection signals to determine values for fuel properties associated with the fuel sample 8, according to an embodiment of the invention. The processor 50 illustrated in FIG. 5 contains a correlating means 62, a multiplying means 64, a summing means 66 and an optional determination means 68.

In the practice of the invention, detected absorbance signal outputs from the detectors 48 can be fed into the processor 50 for determining the values for the properties of the sample. Inside the processor 50, the correlating means 62 can correlate the detected absorbance values (e.g., $A_1+A_2+\ldots A_{17}$) associated with the particular fuel components with a matrix of pre-determined coefficients (e.g., $C_1+C_2+\ldots C_{17}$) associated with the fuel components and pre-determined values of the fuel property being measured. For example, an absorbance value (e.g., $A_1$) associated with MEOH can be correlated with a pre-determined coefficient (e.g., $C_{1di}$) associated with methanol and driveability index. The multiplying means 64 can multiply the detected absorbance values by the correlated pre-determined coefficients to obtain a plurality of absorbance-coefficient products. The summing means 66 can then determine the fuel property associated with the sample by summing the resulting absorbance-coefficient products. For example, the driveability index of a sample can be determined according to the following equation:

$$\text{Sample Driveability Index} = C_{di1}A_1 + C_{di2}A_2 + \ldots C_{di17}A_{17}$$

In an alternative embodiment of the invention, the correlating means 62 can correlate the detected absorbance values (e.g., $A_1+A_2+\ldots A_{17}$) associated with the fuel components with a matrix of pre-determined coefficients (e.g., $C_{1T10}+C_{2T10}+\ldots C_{17T10}$) associated with the fuel components and pre-determined values of T10. Similarly, the correlating means 62 can correlate the detected absorbance values (e.g., $A_1+A_2+\ldots A_{17}$) associated with the fuel components with matrices of pre-determined coefficients associated with the fuel components and pre-determined values of T50 and T90. The multiplying means 64 can multiply the detected absorbance values by the correlated pre-determined coefficients to obtain a plurality of absorbance-coefficient products. The summing means 66 can then sum the resulting absorbance-coefficient products to determine the $T_{10}$, $T_{50}$ and $T_{90}$ values associated with the sample according to the following equations:

$$\text{Sample } T10 = C_{1T10}A_1 + C_{2T10}A_2 + \ldots C_{17T10}A_{17}$$

$$\text{Sample } T50 = C_{1T50}A_1 + C_{2T50}A_2 + \ldots C_{17T50}A_{17}$$

$$\text{Sample } T90 = C_{1T90}A_1 + C_{2T90}A_2 + \ldots C_{17T90}A_{17}$$

The determination means 68 can determine the driveability index for the sample by inserting the T10, T50 and T90 values determined for the sample into the standard driveability index equation.

In sum, the present invention benefits from the recognition that a select fuel can be simply and relatively inexpensively characterized on-site at a fuel delivery dispenser by using mid-infrared analysis to measure fuel properties, such as driveability index. In addition, the measured values can be compared with the fuel property values specified for the fuel by the fuel company to determine a sample fuel rating. Further, the optimal fuel choice for the vehicle can be identified by comparing the preferred fuel property values for the vehicle based on the vehicle manufacturer's recommendations with the fuel properties for each of the dispenser fuels available. It will be understood that the above description pertains to only several embodiments of the present invention. That is, the description is provided by way of illustration and not by way of limitation. The invention is further characterized according to the following claims:

What is claimed is:

1. A method for determining at least one pre-selected fuel property of a fuel sample comprising the steps of:

measuring on-site at a fuel delivery dispenser a value for the fuel property associated with the sample through mid-infrared analysis;

comparing the measured value with a pre-determined preferred value range for the fuel property; and displaying a result of the comparison step.

2. The method of claim 1, further comprising:

evaluating a fuel sample rating based upon comparing the measured value with the pre-determined preferred value range for the fuel property for the sample; and displaying the fuel sample rating.

3. The method of claim 1, further comprising:

entering vehicle information;

correlating the vehicle information with a pre-determined preferred value range for the fuel property for the vehicle;

comparing the measured value with the pre-determined preferred value range for the fuel property for the vehicle; and displaying a result of the comparison step.

4. The method of claim 3, further comprising:

evaluating a rating of the fuel sample for the vehicle based upon the comparing the measured value with the predetermined preferred value range for the fuel property for the vehicle; and displaying the fuel sample rating.

5. The method of claim 3, further comprising:

correlating the pre-determined preferred value range with a value for the fuel property for each of a plurality of dispenser fuels;

identifying an optimal dispenser fuel for the vehicle based upon a result of the correlating step; and displaying a result of the identifying step.

6. The method of claim 1, wherein the step of measuring on-site the value for the fuel property associated with the sample through mid-infrared analysis further comprises determining a driveability index value.

7. The method of claim 6, wherein the step of measuring on-site the value for the fuel property associated with the sample through mid-infrared analysis further comprises the steps of:

illuminating the sample with mid-infrared light;

detecting a plurality of absorbance values associated with a plurality of fuel components in the sample;

correlating the detected absorbance values with a matrix of a plurality of pre-determined coefficients associated with the fuel components and a plurality of pre-determined T10 values, a matrix of a plurality of pre-determined coefficients associated with the fuel components and a plurality of pre-determined T50 values, and a matrix of a plurality of pre-determined coefficients associated with the fuel components and a plurality of pre-determined T90 values;

multiplying the detected absorbance values by the correlated pre-determined coefficients to obtain a plurality of absorbance-coefficient products; and summing the absorbance-coefficient products to determine a T10 value, a T50 value and a T90 value associated with the sample; and determining the driveability index associated with the sample based upon the determined T10, the T50 and the T90 values.

8. The method of claim 1, wherein the step of measuring on-site the value for the fuel property associated with the sample further comprises the steps of:

illuminating the sample with mid-infrared light;

detecting a plurality of absorbance values associated with a plurality of fuel components in the sample;

correlating the detected absorbance values with a matrix of a plurality of pre-determined coefficients associated with the fuel components and a plurality of pre-determined values of the fuel property;

multiplying the detected absorbance values by the correlated pre-determined coefficients to obtain a plurality of absorbance-coefficient products; and summing the absorbance-coefficient products to determine the value of the fuel property associated with the sample.

9. The method of claim 1, wherein the step of measuring on-site the value for the fuel property associated with the sample through mid-infrared analysis further comprises determining an octane number value.

10. The method of claim 1, wherein the step of measuring on-site the value for the fuel property associated with the sample through mid-infrared analysis further comprises determining a Reid vapor pressure value.

11. An apparatus for determining at least one fuel property of a fuel sample comprising:

a measurement means for measuring on-site at a fuel delivery dispenser a value for at least one pre-selected fuel property associated with the sample through mid-infrared analysis;

a comparison means for comparing the measured value with a predetermined preferred value range for the fuel property; and a display means for displaying a result of the comparison.

12. The apparatus of claim 11, further comprising:

a rating means for evaluating the fuel sample based upon comparing the measured value with the pre-determined preferred value range for the fuel property for the sample; and a display means for displaying a fuel sample evaluation.

13. The apparatus of claim 12, further comprising:

an inputting means for entering vehicle information;

a processing means for correlating the vehicle information with a pre-determined preferred value range for the fuel property for the vehicle;

a comparing means for comparing the measured value with the pre-determined preferred value range for the fuel property for the vehicle; and a display means for displaying a result of the comparison.

14. The apparatus of claim 13, further comprising:

a rating means for evaluating the fuel sample for the vehicle based upon comparing the measured value with the pre-determined preferred value range for the fuel property for the vehicle; and a display means for displaying the fuel sample evaluation.

15. The apparatus of claim 13, further comprising:

an identification means for correlating the pre-determined preferred value range for the fuel property for the vehicle with a value for the fuel property for each of a plurality of dispenser fuels to identify an optimal dispenser fuel for the vehicle; and a display means for displaying the optimal dispenser fuel for the vehicle.

16. The apparatus of claim 12, wherein the measurement means further comprises a driveability index determination means for determining driveability index.

17. The apparatus of claim 16, wherein the driveability index determination means further comprises:

a mid-infrared light source for illuminating the sample;

a detector for detecting a plurality of absorbance values associated with a plurality of fuel components in the sample;

a correlating means for correlating the detected absorbance values with a matrix of a plurality of pre-determined coefficients associated with the fuel components and a plurality of pre-determined T10 values, a matrix of a plurality of pre-determined coefficients associated with the fuel components and a plurality of pre-determined T50 values, and a matrix of a plurality of pre-determined coefficients associated with the fuel components and a plurality of pre-determined T90 values;

a multiplying means for multiplying the detected absorbance values by the correlated pre-determined coefficients to obtain a plurality of absorbance-coefficient products; and a summing means for summing the absorbance-coefficient products to determine a T10 value, a T50 value and a T90 value associated with the sample; and a determination means for determining the driveability index associated with the sample based upon the determined T10, the T50 and the T90 values.

18. The apparatus of claim 11, wherein the measurement means further comprises:

a mid-infrared light source for illuminating the sample;

a detector for detecting a plurality of absorbance values associated with a plurality of fuel components in the sample;

a correlating means for correlating the detected absorbance values with a matrix of a plurality of pre-determined coefficients associated with the fuel components and a plurality of pre-determined values of the fuel property;

a multiplying means for multiplying the detected absorbance values by the correlated pre-determined coefficients to obtain a plurality of absorbance-coefficient products; and a summing means for summing the absorbance-coefficient products to determine the value of the fuel property associated with the sample.

19. The apparatus of claim 11, wherein the measurement means further comprises an octane number determination means for determining octane number.

20. The apparatus of claim 11, wherein the measurement means further comprises a Reid vapor pressure determination means for determining Reid vapor pressure.

21. The apparatus of claim 11, wherein the apparatus is a portable apparatus.

22. The apparatus of claim 11, wherein the apparatus further comprises an integral part of a fuel delivery dispenser.

23. The apparatus of claim 11, wherein the apparatus further comprises a data communication means for communicating with a remote computer.

24. A method for determining at least one pre-selected fuel property of a fuel sample comprising the steps of:

measuring on-site at a fuel delivery dispenser a value for the fuel property associated with the sample through mid-infrared analysis;

entering vehicle information;

correlating the vehicle information with a pre-determined preferred value range for the fuel property for the vehicle;

comparing the measured value with the predetermined preferred value range for the fuel property for the vehicle;

evaluating a rating of the fuel sample for the vehicle based upon the comparing the measured value with the pre-determined preferred value range for the fuel property for the vehicle; and displaying the fuel sample rating.

25. A method for determining at least one pre-selected fuel property of a fuel sample comprising the steps of:

measuring on-site at a fuel delivery dispenser a value for the fuel property associated with the sample through mid-infrared analysis;

entering vehicle information;

correlating the vehicle information with a pre-determined preferred value range for the fuel property for the vehicle;

comparing the measured value with the pre-determined preferred value range for the fuel property for the vehicle;

correlating the pre-determined preferred value range with a value for the fuel property for each of a plurality of dispenser fuels;

identifying an optimal dispenser fuel for the vehicle based upon a result of the correlating step; and displaying a result of the identifying step.

26. An apparatus for determining at least one fuel property of a fuel sample comprising:

a measurement means for measuring on-site at a fuel delivery dispenser a value for at least one pre-selected fuel property associated with the sample through mid-infrared analysis;

an inputting means for entering vehicle information;

a processing means for correlating the vehicle information with a pre-determined preferred value range for the fuel property for the vehicle;

rating means for evaluating the fuel sample for the vehicle based upon comparing the measured value with the pre-determined preferred value range for the fuel property for the vehicle; and a display means for displaying the fuel sample evaluation.

27. An apparatus for determining at least one fuel property of a fuel sample comprising:

a measurement means for measuring on-site at a fuel delivery dispenser a value for at least one pre-selected fuel property associated with the sample through mid-infrared analysis;

an inputting means for entering vehicle information;

a processing means for correlating the vehicle information with a pre-determined preferred value range for the fuel property for the vehicle;

an identification means for correlating the pre-determined preferred value range for the fuel property for the vehicle with a value for the fuel property for each of a plurality of dispenser fuels to identify an optimal dispenser fuel for the vehicle; and a display means for displaying the optimal dispenser fuel for the vehicle.

* * * * *